US005747057A

United States Patent [19]

Miller

[11] Patent Number: 5,747,057
[45] Date of Patent: May 5, 1998

[54] SUSTAINED RELEASE PYRIPROXIFEN COMPOSITIONS FOR PARASITE CONTROL

[75] Inventor: Thomas A. Miller, Fort Worth, Tex.

[73] Assignee: Virbac, Inc., Ft. Worth, Tex.

[21] Appl. No.: 626,001

[22] Filed: Apr. 1, 1996

Related U.S. Application Data

[62] Division of Ser. No. 108,909, Aug. 13, 1993, Pat. No. 5,632,999.

[51] Int. Cl.$^6$ .......................... A01N 25/34; A01N 31/44
[52] U.S. Cl. .................... 424/411; 514/68; 514/86; 514/98; 514/136; 514/318; 514/345; 514/637
[58] Field of Search .................... 514/68, 86, 98, 514/136, 318, 345, 411, 637; 424/411

[56] References Cited

U.S. PATENT DOCUMENTS

| | | | |
|---|---|---|---|
| 4,150,109 | 4/1979 | Dick et al. | 424/411 |
| 4,166,107 | 8/1979 | Miller et al. | 424/19 |
| 4,751,223 | 6/1988 | Glamkowski et al. | 514/219 |
| 4,751,225 | 6/1988 | Nishida et al. | 514/277 |
| 4,879,117 | 11/1989 | Rombi | 424/411 |
| 4,879,292 | 11/1989 | Nishida et al. | 514/241 |
| 4,970,222 | 11/1990 | Nishida et al. | 514/369 |
| 4,973,589 | 11/1990 | Barnett et al. | 514/245 |
| 5,057,527 | 10/1991 | Alig et al. | 514/345 |
| 5,071,860 | 12/1991 | Alig et al. | 514/332 |
| 5,221,535 | 6/1993 | Domb | 424/450 |

FOREIGN PATENT DOCUMENTS

| | | |
|---|---|---|
| 2048543 | 2/1992 | Canada . |
| 2082549 | 5/1993 | Canada . |
| 549441 | 6/1993 | European Pat. Off. . |
| 9209950 | 1/1994 | South Africa . |
| 929950 | 1/1994 | South Africa . |

OTHER PUBLICATIONS

Olsen, Alice "Ovicidal effect on the cat flea, *Ctenocephalides felis* (Bouché), of treating fur of cats and dogs with methoprene" *International Pest Control*, Jan./Feb. 1985, pp. 10–13, 16.

*Primary Examiner*—Kevin E. Weddington
*Attorney, Agent, or Firm*—Martin L. McGregor

[57] ABSTRACT

The invention comprises a composition of matter containing a matrix, a plasticizer and pyriproxifen for controlling fleas.

15 Claims, No Drawings

SUSTAINED RELEASE PYRIPROXIFEN COMPOSITIONS FOR PARASITE CONTROL

This is a divisional of application Ser. No. 08/108,909, filed on Aug. 13, 1993, now U.S. Pat. No. 5,632,999.

BACKGROUND OF THE INVENTION

1. Field of the Invention

The present invention relates to sustained release compositions containing and releasing pyriproxifen, 2-[1-methyl-2-(4-phenoxyphenoxy)ethoxy]pyridine, and the use of such compositions for control of ectoparasitic insects on homoiothermic or warm-blooded animals and in another embodiment, the use of combinations of pyriproxifen with insecticidal and acaricidal toxicant active ingredients in sustained release compositions to control both ectoparasitic insects and ectoparasitic acarines.

2. Background

Blood sucking ectoparasites of the class Insecta include fleas, such as *Ctenocephalides felis* and *Ctenocephalides canis* (cat and dog fleas), as well as lice, mosquitos, tabanids, tsetse and other biting flies and those of the class Aricana include ticks such as Boophilus, Amblyomma, Anocentor, Dermacentor, Haemaphysalis, Hyalomma, Ixodes, Rhipicentor, Margaropus, Rhipicephalus, Argas, Otobius and Ornithodoros and mites. These ectoparasites infest or attack many useful homoiothermic animals, including farm animals such as cattle, swine, sheep, goats, poultry such as chickens, turkeys and geese, fur bearing animals such as mink, foxes, chinchilla, rabbits, and pet animals such as dogs and cats.

Ticks are described as hard ticks or soft ticks and are characterized as one host, two host, or three host ticks. They attach to a suitable host animal and feed on blood and body fluids. Engorged females detach and drop from the host and lay large numbers of eggs (2,000 to 20,000) in a suitable niche in the ground or in some other sheltered location in which hatching occurs. The larvae then seek hosts from which to obtain blood meals. Larvae of one host ticks molt on the host twice to become nymphs and adults without leaving the host. Larvae of two and three host ticks drop off the host, molt in the environment and find a second or third host (as nymph or adult) on which to feed.

Ticks are responsible for the transmission and propagation of many human and animal diseases throughout the world. Ticks of major economic importance include Boophilus, Rhipicephalus, Ixodes, Hyalomma, Amblyomma, and Dermacentor. They are vectors of bacterial, viral, rickettsial and protozoal diseases, and cause tick paralysis and tick toxicosis. Even a single *Ixodes holocyclus* tick can cause paralysis consequent to injecting its saliva into its host in the feeding process. Tick-borne diseases are usually transmitted by multiple-host ticks. Such diseases, including Babesiosis, Anaplasmosis, Theileriosis and Heart Water are responsible for the death and/or debilitation of vast numbers of pet and food animals throughout the world. In many temperate countries, Ixodid ticks transmit the agent of a chronic, debilitating disease, Lyme disease, from wildlife to man and to his pets. In addition to disease transmission, ticks are responsible for great economic losses in livestock production. Losses are attributable not only to death, but also to damage of hides, loss of growth, reduction in milk production, and reduced grade of meat. Although the debilitating effects of tick infestations on animals have been recognized for years and tremendous advances have been made in tick control programs, no entirely satisfactory methods for controlling or eradicating these parasites have been forthcoming, and ticks have often developed resistance to chemical toxicants.

Infestation of pets by fleas has long been a nuisance to pet owners. Because fleas are able to survive and multiply under a wide range of environmental conditions, controlling flea infestation requires a multi-faceted program that must be vigorously applied to achieve any measure of success.

Adult fleas live in the coat of the cat or dog and feed on blood. Male and female fleas mate while still in the animal's coat. When the female flea lays her eggs, the eggs do not adhere to the fur, but fall off and are distributed to the animal's environment. By this mechanism, while the total environment of the pet animal is infested with flea eggs, infestation is greatest in locations where the pet spends most of its time. Eggs hatch to larvae in about two days. There are three larval stages, each lasting about three days. In the last stage, the larva spins a cocoon and transforms into a pupa. Under optimum conditions (i.e., 33° C. and 65% relative humidity), eggs develop through larvae to pupae in about 8–10 days. After a further period of approximately 8 days, the pupae develop into young adult fleas in the cocoon, still dispersed in the pet's environment. These pre-emerged adult fleas wait in their pupae until they sense, by carbon dioxide tension and/or vibrations, the presence of an animal host, and then emerge explosively and jump into the air and onto the passing host.

Under suitable environmental conditions of temperature and humidity, unfed emerged fleas that fail to find a host can survive for some time in the environment, waiting for a suitable host. It thus takes at least three weeks for eggs to develop to pre-emerged adults, able to reinfest a host animal. However, the pre-emerged adults can remain viable in the cocoon for months, as long as one year. In addition, under sub-optimal temperature conditions, it can take 4–5 months for eggs to develop into pupae containing pre-emerged adults.

Fleas require a blood meal in order to become sexually mature and able to reproduce. After their first blood meal, they undergo a shift in metabolism such that they cannot survive for any time off the host. The blood must come from the correct animal and the female flea's appetite requires that she consumes as much as 5 times her body weight of blood each day. The long life cycle, and especially the extended period of pre-emergence dormancy, has made flea control with compounds applied topically to pet animals difficult and not entirely satisfactory. Most topically applied active ingredients have limited residual effect, thus reinfestation by newly-emerged adult fleas from the pet's environment is a constant problem.

Infestation of dogs and cats with fleas has several undesirable effects for the animals and for their owners. Such undesirable effects include local irritation and annoying itching, leading to scratching. A high proportion of pet animals, particularly dogs, become allergic to flea saliva, resulting in the chronic condition known as flea bite allergy (or flea allergy). This condition causes the animal to bite and scratch, leading to excoriation of the skin, secondary pyrogenic infection, hair loss, and chronic severe inflammatory skin changes. Allergic pets may suffer severe skin reactions to the bite of even a few fleas. Furthermore, most dogs and cats that are infested with fleas also become infected with *Dipylidium caninum*, the tapeworm transmitted by fleas.

In prolonged absence of suitable animals, newly emerged fleas attack any mammal, including humans, although they are not capable of full reproductive potential if human blood is their sole source of nutrition. Even in the presence of the pet animal, the owner may be bitten by fleas. Some humans may suffer allergic skin disease as a result of being bitten by dog and cat fleas.

Since, like most insects, fleas can adapt to survive exposure to normal toxic agents, and the tolerance of dogs and cats to chemical agents varies, it is desirable to have a multiplicity of agents and methods available for controlling fleas. Prior art methods have included numerous toxic agents such as organophosphates (e.g., chlorpyrifos), carbamates (e.g., carbaryl), pyrethroids (e.g., natural pyrethrins and synthetic pyrethroids like permethrin), and other topical insecticides formulated and designed to kill the adult flea after their application to the pet. Many of the effective residual action toxic agents against fleas, such as DDT, benzene hexachloride, and other chlorinated hydrocarbon insecticides, have been banned from most countries because of environmental persistence of residues and their effect on certain wildlife. Others have been banned because of long-term health risks, including risks of cancer to chronically exposed humans. In the United States, even currently approved and available toxic agents that are effective against fleas, some only briefly, are under scrutiny because of concerns for long-term health hazards to pets and to their owners. These considerations have limited utility of insecticidal and acaricidal toxic compounds for control of fleas and ticks on pet animals and in their environments, and of ectoparasites on animals in general.

Single topical application of such insecticidal and acaricidal compounds, usually with synergists and repellents, are effective, and to avoid the inconvenience of frequently repeated applications of sprays, dips, pour-ons, shampoos, dusts and other topical delivery formulations, both residual compounds and initial higher dosages of potentially toxic compounds have been employed in formulations to extend the period of activity of single applications, and hence to reduce the frequency of application. However, the most stable residual compounds, (i.e., both toxicants and synergists) and the higher dosages have resulted in widespread toxic reactions in pet animals, including deaths. Some animals, particularly cats through their self-grooming activities, are much more prone to adverse reactions and there are few residual formulations that can be applied safely to the cat. This results in repeated applications that most cats find objectionable and resist vigorously, resulting in poor treatment compliance.

Due to the inconvenience and consequent failure of compliance by pet owners with the repeat treatment protocols that are necessary to achieve successful control of ectoparasites through sprays, pour-ons, dips, shampoos, dusts or other topical applications of toxicants, synergists, repellents and insect growth regulators; and similarly the difficulty of repeated daily oral dosage of tablets or other dose forms containing systemically active compounds for the control of ectoparasites on pet animals, particularly on cats, it is desirable that alternative, more convenient control systems with assured higher treatment compliance be made available.

The difficulty of topical application control methods has led to the development of controlled release devices such as solid plastic collars and medallions and plastic reservoirs containing insecticidal and acaricidal toxicants, some with synergists, in which the active ingredients are either incorporated into the solid plastic matrix or are present as liquid in the reservoir. The toxicants are released from the solid matrixes by diffusion to the surface. Toxicants that are liquid at ambient temperature diffuse through a rate limiting semi-permeable membrane from the plastic reservoir. Toxicants that are solid (e.g., powder) at ambient temperatures dissolve in the plasticizer and in any other liquid lipophilic solvents in the matrix and are by diffusion carried to the surface to become available to spread over the coat of the animal. Liquid toxicants in controlled release reservoir devices diffuse out through semi-permeable membranes and hence become available for spread over the coat of the animal. Toxicants with high vapor pressure (e.g., some organophosphates), when they reach the surface of the controlled release device achieve their insecticidal and acaricidal activities partially by evaporation to spread over the animal surface (and its environment) and partially by solution in the natural oils in the haircoat to spread by diffusion of these oils. Compounds with low vapor pressure (e.g., amitraz and synthetic pyrethroids) are spread only by solution in the oil of the haircoat.

The technology of formulating and manufacturing controlled release devices, such as collars, medallions and reservoirs for delivery of insecticidal and acaricidal toxicant compounds, is well-known in the literature. Topical applications of insect growth regulators generally are found, for example, in U.S. Pat. No. 5,221,535 and references cited therein. However, the insect growth regulators are applied, for example, as sprays that have to be applied repeatedly at intervals of a few days to at most one month. There is no disclosure of using insect growth regulators in sustained release compositions. Thus, the prior art does not suggest the possibility of employing a sustained release device in the topical application of pyriproxifen or pyriproxifen-like compounds.

The technology of formulating and manufacturing controlled release devices such as collars, medallions and reservoirs for the delivery of insecticidal and acaricidal toxicant compounds, is well known in the literature. Insecticide collars generally consist of flexible plastic strips impregnated with insecticide. The usual production of these collars—by extrusion—subjects the insecticide to high temperatures during the extrusion step, often limiting the effectiveness of the collar due to degradation of the insecticide. The insecticide is released from the collar by evaporation of volatile insecticides or by diffusion in the case of non-volatile insecticides. Highly volatile insecticides are of course, sensitive to heat degradation, while a large portion of the non-volatile compounds remain trapped in the polymer of the plastic collar.

U.S. Pat. No. 4,879,117 by Rombi teaches a novel design for a collar which contains a central core of porous material impregnated with insecticide and plasticizer. The core is then covered with a thin polymer. The plasticizer aids the insecticide in diffusing through the polymer to the animal, [p. 3, lines 5–14]. The advantage of this collar is that retention of the active ingredient is greatly reduced. However, since the majority of collars are currently made by extrusion processes, this process requires retooling of the manufacturing plant to accommodate this more complex manufacturing process. Although Rombi '117 generally discloses the use of insect growth regulators with the disclosed device, there is no suggestion that high molecular weight insect growth regulator type materials can be used in a conventional collar design, nor is there any suggestion that pyriproxifen could be successfully formulated for sustained release.

U.S. Pat. No. 4,150,109 by Dick et al. employs the insecticides Diazinone and Diazoxone in conjugation with plasticizers and vegetable oils in heat extruded plastic collars. The insecticide is present in the collar at concentrations of 10–20%, (p. 31, lines 11–35). The plasticizer contained in the collar aids in the diffusion of the insecticide through the polymer of the collar to the animal. However, Dick does not suggest use of insect growth regulator type materials with the plasticizer and stabilizers disclosed therein.

Certain substituted heterocyclics of known insecticidal and ovicidal activity, including pyriproxifen, are disclosed in U.S. Pat. Nos. 4,970,222, 4,879,292 and 4,751,223. However, these nitrogen-containing heterocyclic compounds have not heretofore been suggested as being suitable for incorporation into and release from controlled release devices over long periods to affect administration of these ovicidal agents wherein an ovicidally effective dose is available to the target ectoparasite when the target ectoparasite first climbs or jumps onto the host and for months thereafter, and at low, continuous, constant, effective dosage.

The pyriproxifen and related molecules are disclosed, for example, in Nishida et al., U.S. Pat. No. 4,970,222. Nishida teaches the use of this class of compounds in the treatment of the Coleoptera, Lepidoptera, Hemiptera, Dictyoptera and Diptera orders of the class Insecta and the spider mite Tetranychidae belonging to the order Acarina of the class Arachnida. Nishida provides working examples for the control of the wax moth, [p. 49, lines 24, 37], the common mosquito, [p. 49, lines 52–54, p. 51, lines 65–66, and p. 52, lines 5–20], the common housefly, [p. 53, lines 64, 65 and p. 54, lines 24–31], and carmine spider mites, [p. 53, lines 36, 54–60]. Methods of treatment include the use of compositions in the form of emulsifiable concentrates, dusts, granules, wettable powders and fine granules, [p. 45, lines 45–49], which can be applied through means such as spraying, smoking, soil treatment, or in combination with animal feed, [p. 47, lines 26–28]. Nishida does not contemplate the use of pyriproxifen or pyriproxifen-like compounds in the control of flea or tick infestations. Neither are topical applications to phyla other than the Arthropoda listed above recognized.

U.S. Pat. No. 4,973,589 by Barnett et. al. teaches the systemic use of insect growth regulators for the control of fleas only, where the compounds are administered orally, parenterally or by implant, [p. 15, lines 50–55]. Barnett does not describe the use of the pyriproxifen-related compounds. U.S. Pat. No. 4,166,107 by Miller et al. teaches the systemic use of the insect growth regulators methoprene and diflubenzuron in sustained release bolus formulations for the control of livestock pests.

The existing technology referenced above has not heretofore been employed for sustained low level controlled release of the 2-pyridine class of insect growth regulators for topical application to pet animals to achieve control of ectoparasitic insects through sterilization of these ectoparasitic insects and their eggs (when laid on the host). The low solubility, relatively large molecule and relatively low vapor pressure of pyriproxifen compared with some insecticidal and acaricidal toxicants, have led to predictions that formulation of effective controlled release devices for delivery of insect growth regulators at constant ovicidally effective low doses would be difficult. Consequently, ovicidal activity in a target species has been reported for only for methaprene in sustained release type materials.

SUMMARY OF THE INVENTION

It has now been found that surprisingly, pyriproxifen, from the class of heterocyclics disclosed in U.S. Pat. Nos. 4,970,222, 4,879,292 and 4,751,223, can be formulated for sustained release to the haircoat of an animal in such a way that the animal is protected against ectoparasites. Pyriproxifen, 2-[1-methyl-2-(4-phenoxyphenoxy)ethoxy] pyridine, is commercially available from the Sumitomo Chemical Company or from McLaughlin, Gormley, King Co. under the trademark NYLAR$^R$. It has been found that pyriproxifen is effective for controlling ectoparasites in homoiothermic (warm-blooded) animals when administered topically in very low doses. In the examples below, pyriproxifen compositions demonstrate a powerful ovicidal effect toward ectoparasites. As used herein, the term ectoparasite has its normal meaning in the art and includes fleas, ticks, lice, mosquitos, tabanids, tsetse and other biting flies, and especially the species named above. The invention provides sustained release pyriproxifen compositions of matter and methods for using sustained release pyriproxifen compositions to control ectoparasites. The sustained release composition of matter which in percentages of the weight of the total composition comprises:

a. from 10% to 90% of matrix b. from 5% to 40% of plasticizer c. from 0.001 to 5% pyriproxifen.

The compositions may optionally include an insecticidally or acaricidal effective amount of one or more toxicant agents.

DETAILED DESCRIPTION OF THE INVENTION

In the method of the present invention, ectoparasites are exposed to an ovicidally effective amount of the active ingredient when they first climb on to an animal which has been treated by being fitted with a controlled release device delivering a continuous effective dose of the ovicidal active ingredient. The device may be designed to deliver the ovicidally-active ingredient at a daily dose rate of 0.01 mcg/kg to about 1 mg/kg, more preferably about 0.1 mcg/kg to about 100 mcg/kg, and most preferably about 1 mcg/kg to about 50 mcg/kg, where kg expresses the weight of the animal in kilograms.

In an additional preferred embodiment, ovicidally effective amounts in the above stated ranges of pyriproxifen may be combined with effective amount(s) of insecticidal and/or acaricidal toxicant agent(s), for instance, an organophosphate such as diazinon, a carbamate such as bendiocarb, a formamidine such as amitraz or a synthetic pyrethroid such as permethrin. The insecticidal and acaricidal toxicants may also be synergized by including in the controlled release device an insecticide/acaricide synergist such as piperonyl butoxide or n-octyl bicycloheptene dicarboximide. The action of the controlled release device may further be improved by the inclusion also of an insect repellent such as di-n-propyl isocinchomeronate. The toxicants may be present in the controlled release device at concentrations (weight/weight) of 1% to about 30%, more preferably 5% to about 25% and most preferably 8% to 20%.

It is an essential feature of the present invention that the active compound is released from the controlled release device in such a manner that when the ectoparasite first climbs on to the animal, it can come in contact with the active compounds which can then exert activity against both the parasite and its eggs. As used herein, "host" means host animal whose haircoat is normally coated with natural oils, which natural oils serve to solubilize the active ingredients released from the controlled release device and to spread the active ingredients across the entire surface of the animal's haircoat. As used herein, "ovicidally effective" means an effect which leads to a reduced rate of hatching of eggs or to the inability of the male to fertilize the eggs, resulting in sterile egg production. As used herein, insecticidal and/or acaricidal toxicant means a compound which, when released by the controlled release device and spreading over the haircoat of the animal in its natural haircoat oils, is available through contact and/or vapor pressure to the ectoparasite as soon as it climbs on to the host and which toxicant is capable of intoxicating and killing the ectoparasite on contact with the haircoat by the toxicant penetrating the cuticle of or being groomed off the cuticle of the ectoparasite by its grooming activities or the vapor of which toxicant is inhaled by the ectoparasite through its respiratory spiracles.

In accordance with the present invention, introduction of ovicide and toxicant at effective levels can be achieved by controlled release compositions that may be used to form solid devices such as collars and medallions or with hollow devices such as reservoirs with semi-permeable controlled rate membranes, or other devices which release at a controlled rate the active ingredient(s) incorporated therein during manufacture. In this case, the term "formulated" means in the form of a solid or hollow composition suitable for administering an effective amount of the active ingredient(s). Controlled release action of the compositions can be obtained by formulating the active ingredients in matrixes that will both facilitate and physically limit rate of diffusion of the active ingredients from the body of the device to its surface where it becomes available to spread over the haircoat of the animal. The formulated controlled release device is attached to the animal by buckling, by lanyard, by attachment to its haircoat or by attachment to the animal's restraining collar. Especially preferred sustained release compositions are disclosed in the co-pending application Ser. No. 07/634,848 of Durrieu, filed Dec. 27, 1990 now abandoned. Durrieu's application discloses general compositions that have now been found to be effective for sustained release of pyriproxifen.

Matrix formulations now known in the art are formulated as plastics from, for instance, silicones, polyvinyl chloride, polyethylene, polypropylene or other suitable thermoplastic substances. In terms of the total composition, the matrix may comprise from 10% to 90%, preferably between 30% to 70%, and most preferably between 40% and 65%. Plasticizers in a wide variety and appropriate for each of the plastics and selected for their ability to facilitate diffusion of the active ingredients may include, but are not limited to, the adipates, phthalates and citrates, for instance, di-octyl adipate, di-isobutyl adipate, di-isodecyl adipate, di-butyl phthalate, di(C7,9-alkyl) phthalate, di(C7-alkyl) phthalate, di(C9-alkyl) phthalate and acetyl tributyl citrate. In terms of the overall weight of the final composition, plasticizers will be present as 5% to 45%, preferably 10% to 40%, and most preferably from 12% to 30%. The controlled release device formulations may also contain lubricants and stabilizers such as calcium stearate, calcium-zinc stearate complexes, or other stearate compounds. Stabilizers make up from 0.5% to 10%, preferably from 1% to 5%, and most preferably from 2% to 4% of the total weight of the composition. The formulation may also contain an effective amount of antioxidants and preservatives such as butylated hydroxytoluene, butylated hydroxyanisole and for translucent plastics, UV light absorbers such as p-amino benzoic acid, resorcinols such as benzoresorcinol, benzene sulfonic acids such as sulfobenzone and synthetic paramino benzoate salts such as glyceryl p-amino benzoate and 4-(dimethyl amino) benzoic acid. The formulation may also contain stabilized oleaginous substances that serve as lubricants and plasticizers and as solvents for the lipophilic, hydrophobic active ingredients. Examples of suitable oleaginous stabilizers and solvents include a wide variety of stabilized or epoxidized vegetable oils. The formulation may also contain inert mineral salt fillers. To improve the appearance of the devices and to enable identification by brand, target species and active ingredient, colorants are often included in the plastic formulations. Colorants are well-known and include the phthalocyanines, spinels, thioindigoids and anthraqinone families of pigments. To discourage the pet animal or any cohabiting animal from chewing, licking or eating the controlled release device, taste aversion agents may be incorporated into the matrix. Suitable taste aversion agents will depend on the species of animal that it is desired to discourage and could include denatonium benzoate, or denatonium saccharate. Taste aversion agents are 0.005 to 0.5%, preferably 0.01 to 0.3%, most preferably from 0.01% to 0.1% of the total weight of the composition.

The present invention is a method of controlling ectoparasites which comprises continuously administering to the haircoat of a homeothermic animal an ovicidally effective amount of 2-[1-methyl-2-(4-phenoxyphenoxy)ethoxy] pyridine.

The present invention also relates to a method for preventing the propagation of fleas on an animal having a haircoat comprising attaching a controlled release device which releases an ovicidally effective amount of pyriproxifen by diffusion from the surface of the controlled release device into the natural oils on the haircoat of the animal whereby an ovicidally effective amount of pyriproxifen is available for immediate contact with fleas in the animals haircoat. The compound is conveniently released from the controlled release device in a dose of about 0.01 mcg/kg to about 1 mcg/kg, preferably about 0.1 mcg/kg to 100 mcg/kg and most preferable about 1 mcg/kg to about 50 mcg/kg body weight, based on the host animal.

The formulation of the controlled release device or structure of the controlled rate membrane of a reservoir device is designed to provide this continuous release over a suitable period when attached to the animal, preferably from one month to 18 months, more preferably between three months and twelve months, and most preferably for five to nine months. The controlled release device is so formulated that all active ingredient is released at an effective rate over the useful life of the device and that when the device has ceased functioning and is discarded, there is negligible residual active ingredient, thus protecting the environment from potential contamination.

The purpose of the single ovicidal active-containing controlled release device is to be worn continuously by the host animal extending in time over the entire flea season during which climatic and ambient conditions are suitable for the flea life cycle. It is furthermore desirable that the controlled release device be attached before the start of the flea season, with the objective of preventing the first fleas that may climb onto the host from ever producing any fertile eggs that would otherwise contribute to environmental flea reinfestation potential. This provides the advantage that, except for the rare flea and, more importantly, its eggs that may be carried into the treated animal's environment on an untreated uncontrolled dog or cat, which eggs being fertile will develop into new fleas to present an infestation potential to the treated animal and, except for any flea that may be picked up by the treated pet animal when exercising out of its own environment, the animal will therefore never serve as a source of its own reinfestation through contamination of its own environment. This largely obviates the need for repeated topical application to the pet of large doses of potentially toxic insecticides, as is required when the flea population normally builds up in its environment. The further advantage of the controlled release device releasing an ovicidally effective active is to obviate the need for treatment of the animal's environment with insecticidal and acaricidal toxicants, including the indoor quarters shared with its human family and the pet's outdoor environment in its kennel, yard or garden, since such environmental insecticidal/acaricidal treatments are normally poorly effective in controlling the free-living stages of the flea but, more importantly, have the disadvantage of adversely affecting non-target and beneficial insect species in the outdoor environment. When the pet wears the ovicidally effective device year-round, only a light occasional topical treatment of the pet with toxicant-containing products may be required should the pet be flea allergic and react to the rare flea that it may acquire accidentally as explained above.

In the method of the present invention, the controlled release device releasing the ovicidally effective active may also contain and release insecticidal and/or acaricidal toxicants and synergists. While the ovicidal active may be released for a long period of time (e.g., up to one year), the duration of release of the toxicants may be conveniently limited in order to provide immediate protection against the biting of external parasites when the free-living stages of these parasites are already present in large numbers in the animal's environment and climb onto the animal or when the animal is first introduced to such an environment. The addition in the formulation and release from the controlled release device of acaricidal toxicants is particularly beneficial on pet animals, particularly dogs of sporting breeds that are exposed to the environment of other pets or wild mammals in which acarines, particularly ticks, are plentiful, since the ovicidally effective active ingredient may have only limited or negligible effect against the adults and eggs of acarines. A combination ovicide-toxicant controlled release device that would be particularly appropriate for these circumstances is one containing the ovicidally effective active ingredient and a formamidine, for instance amitraz, which acts as a feeding inhibitor on ticks and thus not only protects the animal from tick bites, but from the risk of becoming infected by a tick transmitted disease such as Lyme Borelliosis, Rocky Mountain Spotted Fever, Q Fever, and other rickettsial agents. The following examples illustrate the invention described herein, but do not limit its scope in any way.

EXAMPLE NUMBER 1

Insect Growth Regulator Alone for 150 Days
Residual Activity on Cats

Flea sterilizing collar containing 0.16% pyriproxifen, designed to be attached to a 4 kg cat and to release each day, over 150 consecutive days, 20 mcg pyriproxifen per kg cat body weight.

Each collar weighs 8 gm. Batch of 1000 collars.

| Composition | % | Amount (kg) | A.I./collar |
|---|---|---|---|
| Pyriproxifen technical @ 92% | 0.16% | 0.013 | 13.04 mg |
| Polyvinyl Chloride | 72.8% | 5.827 | |
| Di-octyl Adipate | 20.0% | 1.600 | |
| Calcium Stearate | 2.0% | 0.160 | |
| Vegetable Oil | 5.0% | 0.400 | |

The ingredients are mixed together while being heated to a temperature that results in a viscous homogeneous liquid. For extruded collars, this liquid is forced through an orifice into a cool inert liquid, the ribbon of solidifying plastic being drawn out continuously, cooled and cut into 30 cm lengths. For injection molded collars, the liquid formulation is injected into a mold which is cooled, opened and the individual collars ejected. Buckles are attached to the ends and the individual collars are then coiled and sealed in a pouch or in a preformed transparent plastic container. Final outer packaging, printed with precautionary statements and directions for use, contains the product and its immediate container. When attached around the neck of a flea-infested cat, the existing fleas are sterilized within 3 days and for the next 5 months, all new fleas that may climb onto the cat are immediately sterilized.

EXAMPLE NUMBER 2

Insect Growth Regulator Only for 300 Days
Residual Activity on Dogs

Flea sterilizing collar containing 0.16% pyriproxifen, designed to be attached to a dog weighing 20 kg and to release each day, over 300 days, 5 mcg pyriproxifen per kg dog body weight.

Each collar weighs 20 gm. Batch of 1000 collars.

| Composition | % | Amount (kg) | A.I./collar |
|---|---|---|---|
| Pyriproxifen technical @ 92% | 0.16% | 0.033 | 32.6 mg |
| Polyvinyl Chloride | 67.8% | 13.567 | |
| Di-octyl Adipate | 25.0% | 5.000 | |
| Calcium Stearate | 2.0% | 0.400 | |
| Vegetable Oil | 5.0% | 1.000 | |

The ingredients are mixed together while being heated to a temperature that results in a viscous homogeneous liquid. For extruded collars, this liquid is forced through an orifice into a cool inert liquid, the ribbon of solidifying plastic being drawn out continuously, cooled and cut into 65 cm lengths. For injection molded collars, the liquid formulation is injected into a mold, which is cooled, opened and the individual collars ejected. Buckles are attached to the ends, the individual collars are then coiled and sealed in a pouch or in a preformed transparent plastic container. Final outer packaging, printed with precautionary statements and directions for use, contains the product and its immediate container. When attached around the neck of a flea-infested dog, the existing fleas are sterilized within 3 days and for the next 10 months, all new fleas that may climb onto the dog are immediately sterilized.

EXAMPLE 3

Insect Growth Regulator and Insecticidal Toxicant
for 150/90 Days Residual Activity on Cats Flea Killing and Sterilizing Collar, containing 0.09% pyriproxifen and 8% permethrin, designed to be attached to a 4 kg cat and to release, per kg of cat body weight each day 20 mcg of pyriproxifen over 150 days, and 1.1 mg of permethrin over 90 days.

Each collar weighs 15 gm. Batch of 1000 collars.

| Composition | % | Amount (kg) | A.I./collar |
|---|---|---|---|
| Pyriproxifen technical @ 92% | 0.09% | 0.013 | 13.04 mg |

-continued

| Composition | % | Amount (kg) | A.I./collar |
|---|---|---|---|
| Permethrin @ 93% | 8.00% | 1.29 | 129 gm |
| Polyvinyl Chloride | 64.30% | 9.66 | |
| Di-octyl Adipate | 20.00% | 3.000 | |
| Calcium Stearate | 2.00% | 0.300 | |
| Vegetable Oil | 5.00% | 0.750 | |

The ingredients are mixed together while being heated to a temperature that results in a viscous homogeneous liquid. For extruded collars, this liquid is forced through an orifice into a cool inert liquid, the ribbon of solidifying plastic being drawn out continuously, cooled and cut into 30 cm lengths. For injection molded collars, the liquid formulation is injected into a mold, which is cooled, opened and the individual collars ejected. Buckles are attached to the ends and the individual collars are then coiled and sealed in a pouch or in a preformed transparent plastic container. Final outer packaging, printed with precautionary statements and directions for use, contains the product and its immediate container. When attached around the neck of a flea-infested cat, most pre-existing fleas are killed within 24 hours, any survivors are sterilized within 3 days and for the next 3 months, most new fleas are killed within a few hours and all surviving fleas are immediately sterilized until 5 months after collar attachment.

EXAMPLE NUMBER 4

Insect Growth Regulator and Insecticidal Toxicant for 180/90 Days Residual Activity on Dogs Flea and Tick Killing and Flea Sterilizing Collar, containing 0.07% pyriproxifen and 18% permethrin, designed to be attached to a 20 kg dog and to release, per kg of dog body weight each day 5 mcg of pyriproxifen over 180 days, and 0.3 mg of permethrin over 90 days.

Each collar weighs 30 gm. Batch of 1000 collars.

| Composition | % | Amount (kg) | A.I./collar |
|---|---|---|---|
| Pyriproxifen technical @ 92% | 0.07% | 0.020 | 19.57 mg. |
| Permethrin @ 93% | 18.00% | 5.81 | 5.81 gm |
| Polyvinyl Chloride | 53.57% | 16.07 | |
| Di-octyl Adipate | 20.00% | 6.000 | |
| Calcium Stearate | 2.00% | 0.600 | |
| Vegetable Oil | 5.00% | 1.500 | |

The ingredients are mixed together while being heated to a temperature that results in a viscous homogeneous liquid. For extruded collars, this liquid is forced through an orifice into a cool inert liquid, the ribbon of solidifying plastic being drawn out continuously, cooled and cut into 65 cm lengths. For injection molded collars, the liquid formulation is injected into a mold which is cooled, opened and the individual collars ejected. Buckles are attached to the ends and the individual collars are then coiled and sealed in a pouch or in a preformed transparent plastic container. Final outer packaging, printed with precautionary statements and directions for use, contains the product and its immediate container. When attached around the neck of a flea or tick infested dog, most pre-existing fleas are killed within 24 hours and ticks in 2 days, any surviving fleas are sterilized within 3 days. For the next 3 months, most new fleas and ticks are killed within a few hours and all surviving fleas are immediately sterilized until 6 months after collar attachment.

EXAMPLE NUMBER 5

Insect Growth Regulator and Toxicant for 300/150 Days Residual Activity on Dogs

Flea Sterilizing and Insecticidal-Acaricidal Toxicant Collar containing 0.05% pyriproxifen and 10% bendiocarb, designed to be attached to a dog weighing 20 kg and to release, per kg body weight each day, 5 mcg pyriproxifen over 300 days, and 33 mg bendiocarb over 150 days.

Each collar weighs 30 gm. Batch of 1000 collars.

| Composition | % | Amount (kg) | A.I./collar |
|---|---|---|---|
| Pyriproxifen technical @ 92% | 0.05% | 0.033 | 15.0 mg |
| Bendiocarb @ 96% | 10.00% | 3.125 | 3.0 gm |
| Polyvinyl Chloride | 57.53% | 17.259 | |
| Di-isodecyl Adipate | 25.00% | 7.500 | |
| Calcium Stearate | 2.00% | 0.600 | |
| Vegetable Oil | 5.00% | 1.500 | |

The ingredients are mixed together while being heated to a temperature that results in a viscous homogeneous liquid. For extruded collars, this liquid is forced through an orifice into a cool inert liquid, the ribbon of solidifying plastic being drawn out continuously, cooled and cut into 65 cm lengths. For injection molded collars, the liquid formulation is injected into a mold, which is cooled, opened and the individual collars ejected. Buckles are attached to the ends and the individual collars are then coiled and sealed in a pouch or in a preformed transparent plastic container. Final outer packaging, printed with precautionary statements and directions for use, contains the product and its immediate container. When attached around the neck of a flea-infested dog, the pre-existing fleas are killed by the bendiocarb within 24 hours and any survivors are sterilized by the pyriproxifen within 3 days. Because of the inclusion of the toxicant, bendiocarb, for the first 150 days, most new fleas are killed within a few hours and for the entire 300 days, any surviving fleas are immediately sterilized by the pyriproxifen.

EXAMPLE 6

Insect Growth Regulator and Acaricidal Toxicant 150/90 Days Residual Activity on Dogs Flea Sterilizing and Acaricidal Collar containing 0.04% pyriproxifen and 9.0% amitraz, designed to be attached to a dog weighing 20 kg and to release each day per kg body weight, 5 mcg pyriproxifen over 150 days and 30 mg amitraz over 90 days.

Each collar weighs 30 gm. Batch of 1000 collars.

| Composition | % | Amount (kg) | A.I./collar |
|---|---|---|---|
| Pyriproxifen technical @ 92% | 0.04% | 0.016 | 16.3 mg |
| Amitraz technical @ 96% | 9.00% | 3.938 | 3.8 gm |
| Polyvinyl Chloride | 58.58% | 24.605 | |
| Di-isodecyl Adipate | 25.00% | 10.500 | |
| Calcium Stearate | 2.00% | 0.840 | |
| Vegetable Oil | 5.00% | 2.100 | |

The ingredients are mixed together while being heated to a temperature that results in a viscous homogeneous liquid. For extruded collars, this liquid is forced through an orifice into a cool inert liquid, the ribbon of solidifying plastic being drawn out continuously, cooled and cut into 65 cm lengths. For injection molded collars, the liquid formulation is injected into a mold, which is cooled, opened and the individual collars ejected. Buckles are attached to the ends and the individual collars are then coiled and sealed in a pouch or in a preformed transparent plastic container. Final outer packaging, printed with precautionary statements and directions for use, contains the product and its immediate container.

When attached around the neck of a flea and tick infested dog, most pre-existing fleas are sterilized within 3 days. Because of the inclusion of the toxicant amitraz, the feeding action of most pre-existing ticks stops, they detach, fall off and die. For the following 3 months, most new ticks that climb onto the dog are also prevented from feeding when they fall off and die. Concurrently, the continuous release of pyriproxifen immediately sterilizes all new fleas that may climb onto the dog. This action continues over the next 5 months.

EXAMPLE 7

Insect Growth Regulator and Toxicant 150/90 Days Residual Activity on Cats

Flea Sterilizing and Insecticidal-acaricidal Collar containing 0.11% pyriproxifen and 10% diazinon, designed to be attached to a cat weighing 4 kg and to release each day per kg body weight 20 mcg pyriproxifen over 150 days and 13 mg diazinon over 90 days.

Each collar weighs 12 gm. Batch of 1000 collars.

| Composition | % | Amount (kg) | A.I./collar |
|---|---|---|---|
| Pyriproxifen technical @ 92% | 0.11% | 0.014 | 13.0 mg |
| Diazinon @ 87% | 10.00% | 1.379 | 1.2 gm |
| Polyvinyl Chloride | 60.49% | 7.259 | |
| Di-isobutyl Adipate | 25.00% | 3.000 | |
| Calcium Stearate | 1.50% | 0.180 | |
| Vegetable Oil | 1.40% | 0.168 | |

The ingredients are mixed together while being heated to a temperature that results in a viscous homogeneous liquid. For extruded collars, this liquid is forced through an orifice into a cool inert liquid, the ribbon of solidifying plastic being drawn out continuously, cooled and cut into 30 cm lengths. For injection molded collars, the liquid formulation is injected into a mold, which is cooled, opened and the individual collars ejected. Buckles are attached to the ends and the individual collars are then coiled and sealed in a pouch or in a preformed transparent plastic container. Final outer packaging, printed with precautionary statements and directions for use, contains the product and its immediate container.

When attached around the neck of a flea or tick infested cat, most pre-existing fleas and ticks are killed by the diazinon with 24 hours and any surviving fleas are sterilized by the pyriproxifen within 3 days. Because of the inclusion of the toxicant, diazinon, for the first 90 days, most new fleas and ticks are killed within a few hours and for the entire 150 days, any surviving fleas are immediately sterilized by the pyriproxifen.

EXAMPLE 8

Insect Growth Regulator and Toxicant 400/300 Days Residual Activity on Dogs Flea Sterilizing and Insecticidal-Acaricidal Collar containing 0.25% pyriproxifen and 15% diazinon, designed to be attached to a dog weighing 20 kg and to release each day per kg body weight 12 mcg pyriproxifen over 400 days and 21 mg diazinon over 300 days.

Each collar weighs 42 gm. Batch of 1000 collars.

| Composition | % | Amount (kg) | A.I./collar |
|---|---|---|---|
| Pyriproxifen technical @ 92% | 0.25% | 0.113 | 104.3 mg |
| Diazinon @ 87% | 15.00% | 7.241 | 6.3 gm |
| Polyvinyl Chloride | 54.59% | 22.927 | |
| Di-isobutyl Adipate | 25.00% | 10.500 | |
| Calcium Stearate | 1.50% | 0.630 | |
| Vegetable Oil | 1.40% | 0.588 | |

The ingredients are mixed together while being heated to a temperature that results in a viscous homogeneous liquid. For extruded collars, this liquid is forced through an orifice into a cool inert liquid, the ribbon of solidifying plastic being drawn out continuously, cooled and cut into 65 cm lengths. For injection molded collars, the liquid formulation is injected into a mold, which is cooled, opened and the individual collars ejected. Buckles are attached to the ends and the individual collars are then coiled and sealed in a pouch or in a preformed transparent plastic container. Final outer packaging, printed with precautionary statements and directions for use, contains the product and its immediate container.

When attached around the neck of a flea or tick infested dog, most pre-existing fleas and ticks are killed by the diazinon within 24 hours and any surviving fleas are sterilized by the pyriproxifen within 3 days. Because of the inclusion of the toxicant, diazinon, for the first 300 days, most new fleas and ticks are killed within a few hours and for the entire 400 days, any surviving fleas are immediately sterilized by the pyriproxifen.

EXAMPLE 9

Insect Growth Regulator and Synergised Toxicant 150/90 Days Residual Activity Against Fleas on Cats Flea Sterilizing and Synergised Insecticidal Collar containing 0.11% pyriproxifen, 0.45% prallethrin, 2.25% piperonyl butoxide and 2.25% n-octyl bicycloheptene dicarboximide, designed to be attached to cat weighing 4 kg to release each day per kg body weight; 20 mcg pyriproxifen over 150 days and 0.15 mg prallethrin synergised with 0.3 mg each of piperonyl butoxide and n-octyl bicycloheptene dicarboximide, over 90 days.

Each collar weighs 12 gm. Batch of 1000 collars.

| Composition | % | Amount (kg) | A.I. collar |
|---|---|---|---|
| Pyriproxifen technical @ 92% | 0.11% | 0.014 | 13.0 mg |
| Prallethrin @ 92% | 0.45% | 0.059 | 0.1 gm |
| Piperonyl Butoxide | 2.25% | 0.270 | 0.3 gm |
| N-Octyl Bicycloheptene Dicarboximide | 2.25% | 0.270 | 0.3 gm |
| Polyvinyl Chloride | 78.39% | 9.407 | |
| Di-octyl Adipate | 15.00% | 1.800 | |
| Calcium Stearate | 1.50% | 0.180 | |
| Vegetable Oil | 5.0% | 0.400 | |

The ingredients are mixed together while being heated to a temperature that results in a viscous homogeneous liquid. For extruded collars, this liquid is forced through an orifice into a cool inert liquid, the ribbon of solidifying plastic being drawn out continuously, cooled and cut into 30 cm lengths. For injection molded collars, the liquid formulation is injected into a mold, which is cooled, opened and the individual collars ejected. Buckles are attached to the ends and the individual collars are then coiled and sealed in a pouch or in a preformed transparent plastic container. Final outer packaging, printed with precautionary statements and directions for use, contains the product and its immediate container.

When attached around the neck of a flea infested cat, most pre-exiting fleas and ticks are killed by the synergised prallethrin within 24 hours and any surviving fleas are sterilized by the pyriproxifen within 3 days. Because of the inclusion of the synergised toxicant, for the first 90 days, most new fleas are killed within a few hours and for the entire 150 days, any surviving fleas are immediately sterilized by the pyriproxifen.

EXAMPLE 10

Insect Growth Regulator and Synergised Toxicant 150/90 Days Residual Activity Against Fleas and Ticks on Dogs Flea Sterilizing and Synergised Insecticidal Collar containing 0.05% pyriproxifen, 1.8% prallethrin, 9.0% piperonyl butoxide and 9.0% n-octyl bicycloheptene dicarboximide, designed to be attached to dog weighing 20 kg to release each day per kg body weight; 5 mcg pyriproxifen over 150 days and 0.3 mg prallethrin synergised with 1.5 mg each of piperonyl butoxide and n-octyl bicycloheptene dicarboximide, over 90 days.

Each collar weighs 30 gm. Batch of 1000 collars.

| Composition | % | Amount (kg) | A.I./collar |
|---|---|---|---|
| Pyriproxifen Technical @ 92% | 0.05% | 0.018 | 16.6 mg |
| Prallethrin @ 92% | 1.80% | 0.587 | 0.5 gm |
| Piperonyl Butoxide | 9.00% | 2.700 | 2.7 gm |
| N-Octyl Bicycloheptene Dicarboximide | 9.00% | 2.700 | 2.7 gm |
| Polyvinyl Chloride | 63.48% | 19.045 | |
| Di-octyl Adipate | 15.00% | 4.500 | |
| Calcium Stearate | 1.50% | 0.450 | |

The ingredients are mixed together while being heated to a temperature that results in a viscous homogeneous liquid. For extruded collars, this liquid is forced through an orifice into a cool inert liquid, the ribbon of solidifying plastic being drawn out continuously, cooled and cut into 30 cm lengths. For injection molded collars, the liquid formulation is injected into a mold, which is cooled, opened and the individual collars ejected. Buckles are attached to the ends and the individual collars are then coiled and sealed in a pouch or in a preformed transparent plastic container. Final outer packaging, printed with precautionary statements and directions for use, contains the product and its immediate container.

When attached around the neck of a flea and/or tick infested dog, most pre-existing fleas and ticks are killed by the synergised prallethrin within 24 hours and any surviving fleas are sterilized by the pyriproxifen within 3 days. Because of the inclusion of the synergised toxicant, for the first 90 days, most new fleas are killed within a few hours and for the entire 150 days, any surviving fleas are immediately sterilized by the pyriproxifen.

EXAMPLE 11

Flea Control Through Topical Administration of an Active Ingredient

It was first necessary to determine by dose titration the minimum daily application rate of the insect growth regulator, pyriproxifen, that would need to be released from a controlled release device to achieve 100% sterilization of fleas and their eggs. For this technical grade, pyriproxifen, 2-[-1-methyl-2-(-phenoxyphenoxy)ethoxy]pyridine was diluted in a suitable solvent (ethanol) at various active ingredient loads from 0.000045% through 0.5% to provide dose rates over the range of 9 mcg/kg through 97 mg/kg body weight. Twenty dogs and cats that had been pre-infested with fleas and were hence carrying significant burdens of mature fleas that were producing normal fertile ova, were sprayed overall with these formulations until their coats were thoroughly damp to the skin, but stopping short of the point of run-off. Dependent on the species and breed and the length and thickness of the animal's coat, the dosages of liquid spray ranged from 5 to 20 gm/kg. Flea eggs were collected intermittently, at least at weekly intervals, and were incubated under suitable conditions and in suitable media to promote and support egg hatch, larval development and pupation. The dogs and cats were also repeatedly reinfested with newly emerged fleas approximately weekly to maintain their flea burdens. Control dogs and cats were included in the study to monitor the fertility of flea eggs laid by fleas from the same batches as were used to infest and reinfest the treated dogs and cats. Egg fertility was measured by firstly egg hatch and secondly by emergence of adult fleas from their pupae. The duration of 100% flea sterilization after application of the test products varied from as short as one day at the lowest dose rates to in excess of four months at the higher dose rates, at which time the study was discontinued, even though 100% sterility was still observed in the eggs from the animals treated at the highest dose rates. A highly significant correlation was shown between the logarithmically transformed dose rate (mg active ingredient/kg body weight) and duration of ovicidal effect after the single spray application, with the statistical probability of less than 0.001. The regression analysis provided the following graphs from which may be calculated the topical dose rate of active ingredient required to achieve 100% flea egg sterilization for up to three months, including the daily application rate required to induce 100% sterility of all flea eggs laid by fleas on the treated animal.

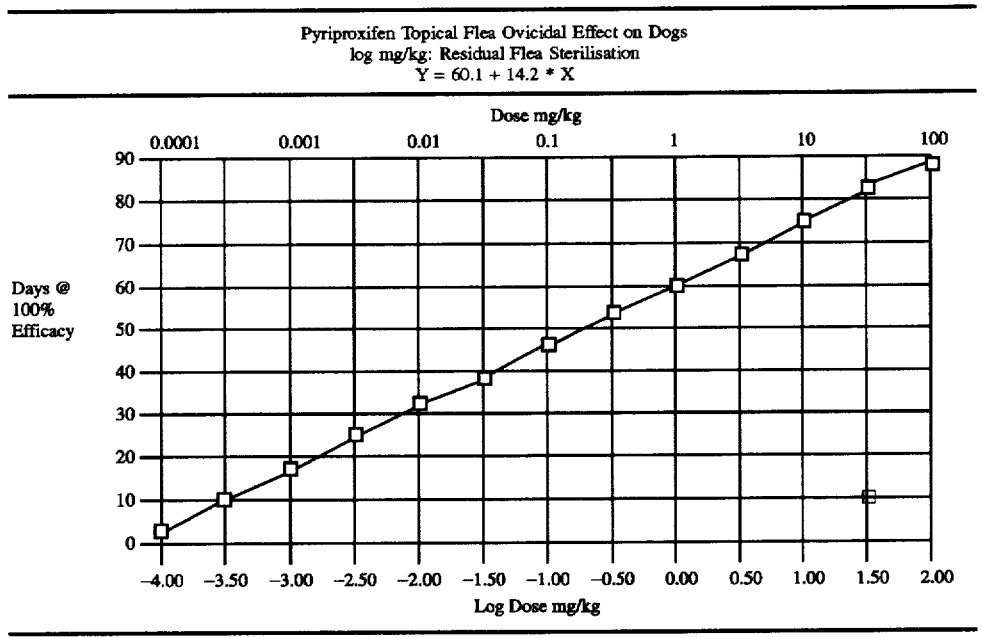

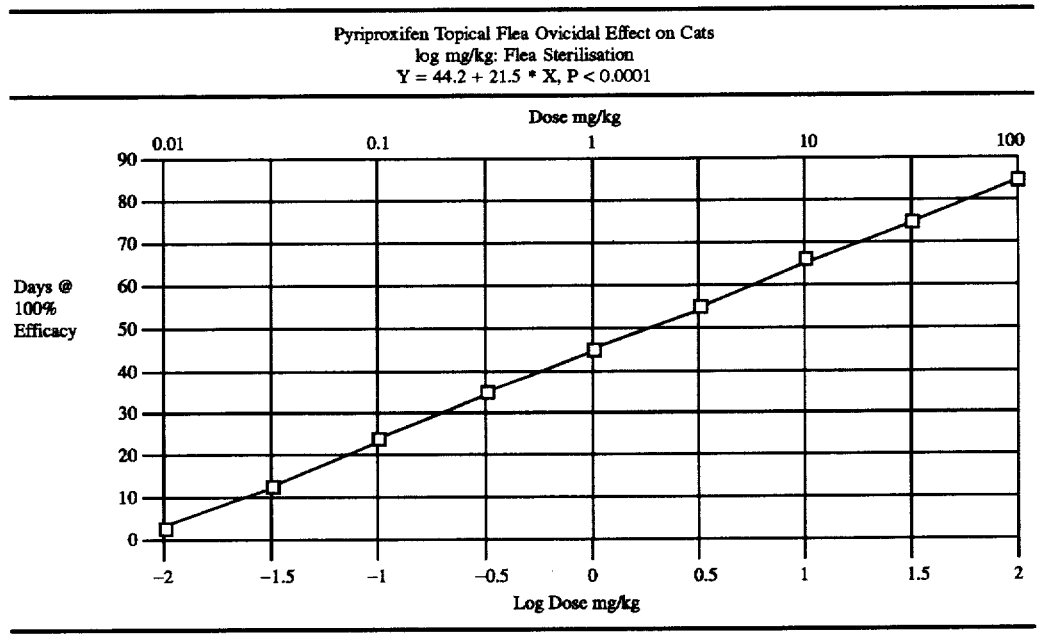

These data show that a suitable daily application rate (i.e., daily ovicidally effective release rate from a controlled release device) would be 10 mcg/kg body weight for cats and less than 0.1 mcg/kg body weight for dogs, the difference between the species being probably related to the excessive grooming habits of cats that remove the ovicidally effective active from their haircoat faster than natural attrition from the haircoat of the dog.

EXAMPLE NUMBER 12

Insect Growth Regulator Alone for 130 Days; Residual Activity on Cats

Flea Sterilizing Collars containing 2.0% pyriproxifen, were attached to three 5 kg cats and released each day, over 120 consecutive days, 7.6 mcg pyriproxifen per kg body weight.

Each collar weighs 8 gm. Batch of 1000 collars.

| Composition | % | Amount (kg) | A.I./collar |
|---|---|---|---|
| Pyriproxyfen technical @ 92% | 2.0% | 0.16 | 147 mg |
| Polyvinyl Chloride | 41.09% | 3.287 | |
| Di-isobutyl Adipate | 12.75% | 1.02 | |
| Butylated Hydroxytoluene | 0.21% | 0.017 | |
| Calcium Stearate | 2.31% | 0.185 | |
| Calcium Carbonate | 40.00% | 3.2 | |
| Vegetable Oil | 1.69% | 0.135 | |

The ingredients are mixed together while being heated to a temperature that results in a viscous homogeneous liquid. For these extruded collars, this liquid was forced through an orifice into a cool inert liquid, the ribbon of solidifying plastic being drawn out continuously, cooled and cut into 30 cm lengths. Buckles were attached to the ends, the individual collars were then coiled and sealed in a pouch or in a multilaminate (paper-aluminum foil-plastic) pouch.

When attached around the neck of the three flea-infested cats, the existing fleas were sterilized within 3 days and for the next 4 months, all new fleas with which the cats were repeatedly reinfested were immediately sterilized. The collars were applied to three cats while three similar untreated cats served as controls. All cats were reinfested several times, each with 100 newly-emerged adult fleas, and the fertility of these fleas were determined by egg hatch and adult emergence. Collars were applied to the three principal cats and flea egg collection was continued for 130 days after application of the collars to the principals. Fertility of the flea eggs was measured by hatch (larvae %) and by adult flea pupation and emergence (adults %). The results were expressed as percent hatch/emergence of the number of eggs incubated on each day and are tabulated below.

Pyriproxifen Collars - Residual Ovicidal Effect on Flea Eggs
Post-Treatment Flea Egg Fertility, Measured by Flea Egg Hatch and/or Adult Flea Emrtgemce   Ins 35.1

| Day after Collar | | 1 | 2 | | 3 | 4 | | 7 | 9 | |
|---|---|---|---|---|---|---|---|---|---|---|
| Attachment | | Adults | Larvae | Adults | Adults | Larvae | Adults | Adults | Larvae | Adults |
| Cat no. | Group | % | % | % | % | % | % | % | % | % |
| 1149 | Treated | 0% | 12% | 21% | 16% | 0% | 0% | 0% | 0% | 0% |
| 1153 | Treated | 44% | 0% | 4% | 0% | 0% | 0% | 0% | 0% | 0% |
| 1154 | Treated | 52% | 16% | 14% | 0% | 0% | 0% | 0% | 0% | 0% |
| Mean group % egg fertility | | 32% | 9% | 13% | 5% | 0% | 0% | 0% | 0% | 0% |
| 1150 | Control | 72% | 84% | 70% | 80% | 56% | 52% | 56% | 80% | 76% |
| 1151 | Control | 72% | 84% | 84% | 16% | 68% | 54% | 60% | 76% | 58% |
| 1152 | Control | 74% | 84% | 76% | 86% | 52% | 66% | 74% | 72% | 86% |
| Mean group % egg fertility | | 73% | 84% | 77% | 61% | 59% | 57% | 63% | 76% | 73% |
| Treatment efficacy | | 56% | 89% | 83% | 91% | 100% | 100% | 100% | 100% | 100% |

| Day | | 25 | 28 | 30 | 44 | 51 | | 53 | 56 | 58 |
|---|---|---|---|---|---|---|---|---|---|---|
| | | Adults | Adults | Larvae | Larvae | Larvae | Adults | Adults | Adults | Adults |
| Cat no. | Group | % | % | % | % | % | % | % | % | % |
| 1149 | Treated | 0% | 0% | 0% | 0% | 0% | 0% | 0% | 0% | 0% |
| 1153 | Treated | 0% | 0% | 0% | 0% | 0% | 0% | 0% | 0% | 0% |
| 1154 | Treated | 0% | 0% | ·0% | 0% | 0% | 0% | 0% | 0% | 0% |
| Mean group % egg fertility | | 0% | 0% | 0% | 0% | 0% | 0% | 0% | 0% | 0% |
| 1150 | Control | 82% | 72% | 68% | 42% | 24% | 30% | 44% | 70% | 58% |
| 1151 | Control | 80% | 76% | 60% | 40% | 22% | 68% | 56% | 68% | 50% |
| 1152 | Control | 72% | 56% | 80% | 36% | 22% | 52% | 46% | 34% | 56% |
| Mean group % egg fertility | | 78% | 68% | 69% | 39% | 23% | 50% | 49% | 57% | 55% |
| Treatment efficacy | | 100% | 100% | 100% | 100% | 100% | 100% | 100% | 100% | 100% |

| Day after Collar | | 11 | 14 | 16 | | 21 | 23 | |
|---|---|---|---|---|---|---|---|---|
| Attachment | | Adults | Adults | Larvae | Adults | Adults | Larvae | Adults |
| Cat no. | Group | % | % | % | % | % | % | % |
| 1149 | Treated | 0% | 0% | 0% | 0% | 0% | 0% | 0% |
| 1153 | Treated | 0% | 0% | 0% | 0% | 0% | 0% | 0% |
| 1154 | Treated | 0% | 0% | 0% | 0% | 0% | 0% | 0% |
| Mean group % egg fertility | | 0% | 0% | 0% | 0% | 0% | 0% | 0% |
| 1150 | Control | 70% | 58% | 56% | 72% | 24% | 80% | 80% |
| 1151 | Control | 60% | 42% | 76% | 42% | 24% | 72% | 58% |
| 1152 | Control | 92% | 60% | 56% | 42% | 46% | 72% | 80% |
| Mean group % egg fertility | | 74% | 53% | 63% | 52% | 31% | 75% | 73% |
| Treatment efficacy | | 100% | 100% | 100% | 100% | 100% | 100% | 100% |

| Day | | 60 | 91 | | 122 | | 130 | |
|---|---|---|---|---|---|---|---|---|
| | | Adults | Larvae | Adults | Larvae | Adults | Larvae | Adults |
| Cat no. | Group | % | % | % | % | % | % | % |
| 1149 | Treated | 0% | 4% | 0% | Terminated | | | |
| 1153 | Treated | 0% | 0% | 0% | 0% | 0% | 0% | 2% |
| 1154 | Treated | 0% | 0% | 0% | 0% | 0% | 0% | 0% |
| Mean group % egg fertility | | 0% | 1% | 0% | 0% | 0% | 0% | 1% |

| Pyriproxifen Collars - Residual Ovicidal Effect on Flea Eggs Post-Treatment Flea Egg Fertility, Measured by Flea Egg Hatch and/or Adult Flea Emrtgemce | | | | | | | | Ins 35.1 |
|---|---|---|---|---|---|---|---|---|
| 1150 | Control | 44% | 28% | 40% | 42% | 50% | 40% | 32% |
| 1151 | Control | 46% | 16% | 80% | 38% | 46% | 46% | 50% |
| 1152 | Control | 22% | 26% | 90% | 38% | 62% | 50% | 22% |
| Mean group % | egg fertility | 37% | 23% | 70% | 39% | 53% | 45% | 35% |
| Treatment efficacy | | 100% | 94% | 100% | 100% | 100% | 100% | 97% |

The results showed that egg fertility was reduced by more than 50% within 24 hours of applying the collars and reached 100% within 96 hours. Complete sterility continued, with one deviation of 94%, for four months. At 130 days, ovicidal efficacy was still 97%.

Collars were removed from the animals at 130 days and analyzed. Comparisons based on the pyriproxifen level in the control collars (that had remained in their sealed package) and the residual levels in the collars taken off the cats at between 3 and 4 months showed that the average daily release rate of pyriproxifen was 7.6 mcg/kg body weight.

I claim:

1. A composition of matter which, in precentages of the weight of the total composition, comprises:
   a. from 10% to 90% matrix;
   b. from 5% to 40% plasticizer;
   c. from 0.001 to 0.04% pyriproxifen.

2. A composition according to claim 1 which comprises from 1% to 30% of an insecticidal or acaricidal toxicant agent.

3. A composition according to claim 1 which comprises from 0.5% to 10% stabilizer.

4. A composition according to claim 1 which comprises an effective amount of an antioxidant.

5. A composition according to claim 2 which comprises from 0.5% to 10% stabilizer.

6. A composition according to claim 2 which comprises an effective amount of an antioxidant.

7. A composition according to claim 2 wherein the toxicant agent is selected from the group consisting of insecticidally active carbamates, insecticidally active organophosphates, acaricidally active formamididines, and insecticidally active pyrethroids.

8. A composition according to claim 2 which comprises a synergist.

9. A composition according to claim 8 wherein the synergist is selected from the group consisting of piperonyl butoxide and n-octyl bicycloheptene dicarboximide.

10. The composition of claim 1 wherein said matrix is selected from the group consisting of silicones, polyvinyl chloride, polyethylene and polypropylene.

11. The composition of claim 10 wherein said matrix further comprises a lubricant selected from the group consisting of vegetable oil, calcium stearate, and calcium-zinc stearate complexes.

12. The composition of claim 4 wherein said antioxidant is selected from the group consisting of butylated hydroxytoluene, butylated hydroxyanisole, p-aminobenzoic acid, benzoresorcinol, sulfobenzene, glyceryl p-amino benzoate and 4-(dimethylamino) benzoic acid.

13. The composition of claim 1 wherein said plasticizer is selected from the group consisting of adipates, phthalates, and citrates.

14. The composition of claim 1 wherein said matrix is shaped to form a collar for an animal.

15. The composition of claim 1 wherein said matrix is shaped to form a medallion for attachment to a collar of an animal.

* * * * *